United States Patent [19]

Frey et al.

[11] Patent Number: 4,961,748
[45] Date of Patent: Oct. 9, 1990

[54] SLEEVE FOR AN ACETABULUM

[75] Inventors: Otto Frey, Winterthur; Rudolf Koch, Berlingen, both of Switzerland

[73] Assignee: Sulzer Brothers Limited, Winterthur, Switzerland

[21] Appl. No.: 393,556

[22] Filed: Aug. 11, 1989

[30] Foreign Application Priority Data

Aug. 24, 1988 [CH] Switzerland ............... 3145/88-3

[51] Int. Cl.$^5$ .............................................. A61P 2/34
[52] U.S. Cl. ..................................................... 623/22
[58] Field of Search ....................... 623/16, 18, 19, 20, 623/22, 23

[56] References Cited

U.S. PATENT DOCUMENTS

| | | | |
|---|---|---|---|
| 3,903,549 | 9/1975 | Deycrle | 623/22 |
| 4,031,570 | 6/1977 | Frey | 623/22 |
| 4,450,592 | 5/1984 | Niederer et al. | 623/22 |
| 4,519,101 | 5/1985 | Schreiber et al. | 623/22 |
| 4,662,891 | 5/1987 | Noiles | 623/22 |
| 4,795,470 | 1/1989 | Goymann et al. | 623/22 |
| 4,834,759 | 5/1989 | Spotorno et al. | 623/22 |
| 4,883,491 | 11/1989 | Mallory et al. | 623/22 |

FOREIGN PATENT DOCUMENTS

| | | |
|---|---|---|
| 0038903 | 11/1981 | European Pat. Off. . |
| 0190981 | 8/1986 | European Pat. Off. . |
| 0242633 | 10/1987 | European Pat. Off. . |
| 0242719 | 10/1987 | European Pat. Off. . |
| 0262379 | 4/1988 | European Pat. Off. . |
| 3630276 | 3/1988 | Fed. Rep. of Germany ........ 623/22 |
| 3726213 | 2/1989 | Fed. Rep. of Germany ........ 623/22 |
| 2592787 | 7/1987 | France . |
| 2622432 | 5/1989 | France ................................. 623/22 |
| 85/00284 | 1/1985 | PCT Int'l Appl. . |
| 0652913 | 12/1985 | Switzerland . |
| 2069338 | 8/1981 | United Kingdom . |

*Primary Examiner*—David J. Isabella
*Attorney, Agent, or Firm*—Kenyon & Kenyon

[57] ABSTRACT

The metal sleeve which is formed with the slot along a generatrix, comprises zones of relatively large wall thickness (D) and zones of relatively reduced wall thickness (d) in alternative relationship around the periphery. The zones of reduced wall thickness are in the form of annular sectors of finite length having parallel walls and radiused transitions into zones of relatively large wall thickness (D). When an insert is pressed in, the sleeve is expanded very uniformly over the entire periphery.

16 Claims, 1 Drawing Sheet

SLEEVE FOR AN ACETABULUM

This invention relates to a sleeve for an acetabulum. More particularly, this invention relates to a metal sleeve for a two-part acetabulum.

As is known, various types of sleeves have been provided for two-part acetabula for cementless fixing in a pelvis. For example, European Patent Application No. 0242633 describes a slotted shell which is adapted to receive an insert which can be press fitted into place. Other types of shells have also been known which employ external threads, such as described in U.S. Pat. No. 4,662,891, United Kingdom Patent Application No. 2,069,338 and European Patent Nos. 0262379 and 0190981. In other cases, the sleeves have been provided with other types of digitated elements for implanting in a bone, such as described in WO85/00284, European Patent No. 0038903 and French Patent No. 2,592,787.

Swiss Patent No. 652,913 describes a frustum-shaped sleeve which is slotted on one side in order to receive an insert which contains an actual shell. In this case, the insert is adapted to be pressed into the hollow interior of the sleeve in a close fit. The cementless fixing of this type of two-part acetabulum, whose sleeve and insert are preferably made of plastics, is effected by expanding the sleeve when the insert is pressed into place. The expansion of the sleeve occurs preferably in that zone of the sleeve periphery which is diametrically opposite the slot. In cases in which the sleeve is made of metal, for example, of pure titanium or a titanium alloy, as has recently become conventional, difficulties arise in connection with the expansion or widening of the sleeve. That is, the metal sleeves are generally required to retain resiliency, for example, to simplify a re-operation. However, during expansion, the metal is stretched beyond the elastic limit within the expansion zone and becomes permanently deformed. Thus, the desired resiliency is lost.

Accordingly, it is an object of the invention to provide a metal sleeve for an acetabulum in which permanent deformations associated with a pressing in of an insert are avoided.

It is another object of the invention to provide a slotted metal sleeve for an acetabulum which can be expanded without permanent deformations taking place therein.

It is another object of the invention to provide a metal sleeve for an acetabulum which can be utilized in reoperations.

Briefly, the invention provides a metal sleeve for an acetabulum which has a frustum-shape with a slot extending on one side from an apex to a base thereof. In addition, the sleeve has a plurality of zones of relatively large wall thickness and a plurality of zones of relatively small wall thickness wherein the two zones alternate peripherally with each other. In addition, each zone of relatively small wall thickness has an annular sector and a transition portion at each end of the sector which merges on a radius into an adjacent zone of relative large wall thickness. This radius is from 0.5 to 1.0 millimeter while each sector has a peripheral length of at least four times the radius.

Providing zones of relatively small wall thickness lead to a distribution over the entire periphery of the sleeve of highly flexible zones which experience expansion or widening. To ensure that this expansion or widening is not limited just to a generatrix of the zones but is distributed over their entire meridian angle (peripheral length), the zones of wall thickness are in the form of annular sectors having parallel boundaries (i.e. walls) of minimum length. The result is that the sleeve expands relatively uniformly over the entire periphery with the expansion in each zone of reduced wall thickness being distributed over the parallel walled part so that stretch limits are never exceeded.

Sleeve stability can be improved if the slot is bounded by zones of relatively large wall thickness. Advantageously, the meridian angles (peripheral length) of the zones of relatively large wall thickness are, in each case, a multiple of those of the zones of reduced wall thickness. The flexibility of the zones of reduced wall thickness can be increased if such zones are reduced in height by recesses which extend from at least one of the end faces (axial ends) into the latter zones.

Advantageously, the wall thicknesses of the sleeve increase from the apex towards the base in order to allow for an increased diameter towards the base and, therefore, an increased deformation torque. Transmission of the sleeve-stressing forces can be improved if at least the wall zones of relatively large wall thickness which bound the slot, and the wall zones disposed opposite the slot-bounding wall zones, have outwardly directed tabs on the base. Conveniently, for fixing the sleeve, the tabs which are diametrically opposite the slot boundaries are formed with through bores for bone screws. To ensure that the sleeve is not expanded beyond a permissible resilient range when a plastic insert is pressed in, the wall zones of relatively large wall thickness at the apex of the frustum can have inwardly directed abutments for the insert. Also, some of these abutments can have, as a means for securing the insert against rotation, spikes which extend towards the base and which penetrate into the plastics insert.

These and other objects and advantages of the invention will become more apparent from the following detailed description taken in conjunction with the accompanying drawings wherein.

Figure 1:
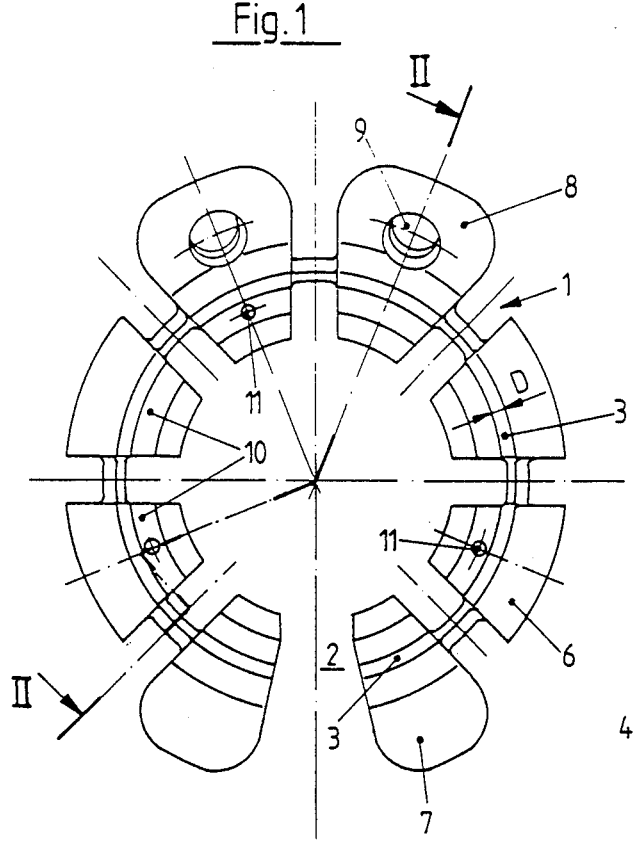
FIG. 1 illustrates a view of sleeve in accordance with the invention taken from the base in the direction of the axis of rotation.

Referring to FIG. 1, the metal sleeve 1 is constructed for use in an acetabulum of two-part construction. That is, the sleeve 1 is intended to receive an insert, such as a plastic insert having a recess for receiving a spherical head (not shown). As indicated, the sleeve 1 is provided with a slot 2 which extends on one side from an apex to a base thereof.

Figure 3:
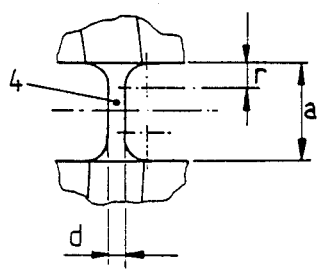
FIG. 3 illustrates an enlarged detailed view of a zone of relatively small wall thickness in accordance with the invention.

The sleeve 1 includes a plurality of zones 3 of relatively large wall thickness D which alternate peripherally with a plurality of zones 4 of relatively small wall thickness d (see FIG. 3).

As illustrated in FIG. 3, each zone 4 of relatively small wall thickness d has an annular sector having parallel walls or boundaries and a transition portion at each end which merges on a radius r into an adjacent zone 3 of relatively large wall thickness. The radius of each transition portion is from 0.5 to 1.0 millimeter while the peripheral length a of each sector is at least four times the radius r.

Figure 2:
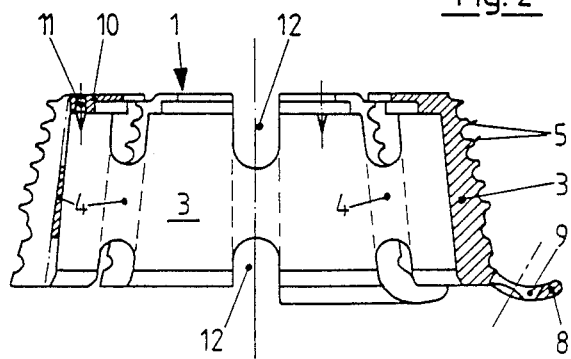
FIG. 2 illustrates a view taken on line II—II of FIG. 1.

As can be gathered from FIG. 2, the zones 4 of relatively small wall thickness d are formed with recesses 12 which extend into such zones from both the end faces of the frustum and which increase the flexibility of the zones 4. The wall thicknesses of the zones 3, 4 in the case of a titanium sleeve can be approximately at the center of the frustum, for example: D=2.5–5 millimeters and d=0.5–2 millimeters.

The wall thicknesses d, D decrease in each zone from the base towards the apex of the frustum. Also, the zones 3 of relatively large wall thickness D have external peripherally extending ribs 5 having a surface structure intended to promote the invasion and ingrowth of tissue. The zones 3 of relatively large wall thickness D have, in the peripheral direction, a circle section (peripheral length) of a greater angle than the zones 4 of reduced wall thickness d and is a multiple of the peripheral length of the zones 4 of small wall thickness. Also, the zones 3 have outwardly extending tabs 6–8 at the base of which the tabs 7 bounding the slots 2 and the diametrically opposite tabs 8 are of larger area than the intermediately disposed tabs 6. The tabs 8 are also formed with throughbores 9 for bone screws (not shown). The function of the tabs 6–8 is to improve the support and fixing of the sleeve 1 in the pelvis.

At the apex, the frustum of the sleeve 1 is terminated in the sections of the zones 3 of relatively large wall thickness D by abutments 10 for the plastics insert (not shown). Individual abutments 10 have spikes 11 which penetrate into the insert when the insert is being pressed in and secure the insert against accidental rotation.

The invention thus provides a metal sleeve which can be peripherally expanded during insertion of an insert during an operative procedure without permanent deformations occurring within the metal sleeve, particularly in the part opposite the slot of the metal sleeve. In addition, the metal sleeve is able to retain a resiliency sufficient to receive inserts in a subsequent re-operation.

What is claimed is:

1. A metal sleeve for an acetabulum having a frustum-shaped shell with a slot extending on one side from a base end to an apex end thereof and splitting said shell, said shell having a plurality of peripheral first zones of relatively large wall thickness and second zones of relatively small wall thickness alternating circumferentially about said shell, each second zone of relatively small wall thickness having an elongated annular sector and a transition portion at each end of said sector merging on a radius into an adjacent first zone of relatively large wall thickness.

2. A sleeve as set forth in claim 1 wherein said radius is from 0.5 to 1.0 millimeter and each sector has a peripheral length at least four times said radius.

3. A sleeve as set forth in claim 1 wherein a pair of said first zones of relatively large wall thickness bound said slot.

4. A sleeve as set forth in claim 1 wherein said first zones of relatively large wall thickness are of a peripheral length equal to a multiple of the peripheral length of said second zones of relatively small wall thickness.

5. A sleeve as set forth in claim 1 wherein each second zone of relatively small wall thickness has a recess at at least one axial end.

6. A sleeve as set forth in claim 1 wherein each zone is of increasing thickness from an apex end thereof to a base end thereof.

7. A sleeve as set forth in claim 1 wherein a pair of first zones of relatively large wall thickness bound said slot and are disposed diametrically opposite a pair of first zones of relatively large wall thickness, each said first zone of said pairs of first zones having an outwardly directed tab thereon.

8. A sleeve as set forth in claim 7 wherein said tabs on said first zones opposite said slot include bores for passage of bone screws therethrough.

9. A sleeve as set forth in claim 1 which further has radially inwardly directed abutments on said first zones of relatively large wall thickness at an apex end thereof.

10. A sleeve as set forth in claim 9 which further comprises a spike extending from at least one abutment towards said base end of said shell.

11. A sleeve for an acetabulum having an annular wall forming a frustum-shape shell with a slot extending from an apex end to a base end thereof and splitting said sleeve, said wall comprising a plurality of peripheral first zones of relatively large wall thickness and second zones of relatively small wall thickness alternating circumferentially about said shell, each second zone of relatively small wall thickness having an elongated annular sector and a transition portion at each end of said sector merging on a radius into an adjacent first zone of relatively large wall thickness.

12. A sleeve as set forth in claim 11 wherein said radius is from 0.5 to 1.0 millimeter and each sector has a peripheral length at least four times said radius.

13. A sleeve as set forth in claim 12 wherein a pair of first zones of relatively large wall thickness bound said slot.

14. A sleeve as set forth in claim 12 wherein each second zone of relatively small wall thickness has a recess at at least one axial end.

15. A sleeve as set forth in claim 12 having an outwardly directed tab on at least one of said first zones.

16. A sleeve as set forth in claim 11 wherein said first zones are of a peripheral length equal to a multiple of the peripheral length of said second zones.

* * * * *